US005625122A

United States Patent [19]
Mak

[11] Patent Number: 5,625,122
[45] Date of Patent: Apr. 29, 1997

[54] MOUSE HAVING A DISRUPTED LCK GENE

[75] Inventor: Tak W. Mak, Toronto, Canada

[73] Assignee: The Ontario Cancer Institute, Toronto, Canada

[21] Appl. No.: 145,043

[22] Filed: Nov. 3, 1993

Related U.S. Application Data

[63] Continuation of Ser. No. 872,985, Apr. 24, 1992, abandoned.

[51] Int. Cl.$^6$ .............................. C12N 5/00; C12N 15/00
[52] U.S. Cl. ................................ 800/2; 435/354; 435/325
[58] Field of Search ............................... 800/2; 435/240.1

[56] References Cited

PUBLICATIONS

Tamauchi et al (1988) Eu. J. Immunol. 18, 1859–1862.
Rouer et al (1989) Gene 84, 105–113.
Bosma et al (1983) Nature 301, 527–530.
Soriano et al (1991) Cell 64, 693–702.
Kappel et al (1992) Current Opinion in Biotechnology 3.548–553.
Abraham et al., "Delayed Thymocyte Development Induced by Augmented Expression of p56$^{lck}$", *J. Exp. Med.* 173:1421–1432 (1991).
Adkins et al., "Total Lymphoid Irradiation Leads to Transient Depletion of the Mouse Thymic Medulla and Persistent Abnormalities Among Medullary Stromal Cells", *The Journal of Immunology*, 140(10):3373–3379 (1988).
Barber et al., "The CD4 and CD8 antigens are coupled to a protein–tyrosine kinase (p56$^{lck}$) that phosphorylates the CD3 complex", *Proc. Natl. Acad. Sci. USA*, 86:3277–3281 (1989).
Blanc et al., "Gene transfer of the Ly–3 chain gene of the mouse CD8 molecular complex: co–transfer with the Ly–2 polypeptide gene results in detectable cell surface expression of the Ly–3 antigenic determinants", *Eur. J. Immunol.*, 18:613–619 (1988).
Bosma et al., "A severe combined immunodeficiency mutation in the mouse", *Nature*, 301:527–530 (1983).
Ameisen et al., "Cell dysfunction and depletion in AIDS: the programmed cell death hypothesis", *Immunology Today*, 12(4):102–105 (1991).
Cobbold et al., "Therapy with monoclonal antibodies by elimination of T–cell subsets in vivo", *Nature*, 312:548–551 (1984).
Cooke et al., "Regulation of T Cell Receptor Signaling by a src Family Protein–Tyrosine Kinase (p59$^{fyn}$)", *Cell*, 65:281–291 (1991).
Cooper, "The SRC Family of Protein–Tyrosine Kinases", *Peptides and Protein Phosphorylation*, Chapter 3:85–113.
Fung–Leung et al., "CD8 Is Needed for Development of Cytotoxic T Cells but Not Helper T Cells", *Cell*, 65:443–449 (1991).
Gorman et al., "Molecular Linkage of the Ly–3 and Ly–2 Genes", *The Journal of Immunology*, 140(10):3646–3653 (1988).

Gossler et al., "Transgenesis by means of blastocyst–derived embryonic stem cell lines", *Proc. Natl. Acad. Sci. USA*, 83:9065–9069 (1986).
Groux, et al., "Activation–induced Death by Apoptosis in CD4$^+$ T Cells from Human Immunodeficiency Virus–infected Asymptomatic Individuals", *J. Exp. Med.*, 175:331–340 (1992).
Joyner et al., "Production of a mutation in mouse En–2 gene by homologous recombination in embryonic stem cells", *Nature*, 338:153–156 (1989).
Kanariou et al., "Immunosuppression with cyclosporin A alters the thymic microenvironment", *Clin. Exp. Immunol.*, 78:263–270 (1989).
Karin et al., "Control of transcription factors by signal transduction pathways: the beginning of the end", *TIBS*, 17:418–422 (1992).
Leist et al., "Functional Analysis of T Lymphoctye Subsets in Antiviral Host Defense", *The Journal of Immunology*, 138:2278–2281 (1987).
Kisielow et al., "Tolerance in T–cell–receptor transgenic mice involves deletion of nonmature CD4$^+$8$^+$ thymocytes", *Nature*, 333:742–746 (1988).
Liaw et al., "Structure, Sequence, and Polymorphism of the LYT–2 T Cell Differentiation Antigen Gene", *The Journal of Immunology*, 137(3):1037–1043 (1986).
MacDonald et al., "Intrathymic deletion of self–reactive cells prevented by neonatal anti–CD4 antibody treatment", *Nature*, 335:174–176 (1988).
Molina et al., "Profound block in thymocyte development in mice lacking p56$^{lck}$", *Nature*, 357:161–164 (1992).
Moskophidis et al., "Mechanism of Recovery from Acute Virus Infection: Treatment of Lymphocytic Choriomeningitis Virus–Infected Mice with Monoclonal Antibodies Reveals that Lyt–2$^+$ T Lymphocytes Mediate Clearance of Virus and Regulate the Antivirual Antibody Response", *Journal of Virology*, 61(6):1867–1874 (1987).
Nakauchi et al., "Molecular Cloning of Lyt–3, a membrane glycoprotein marking a subset of mouse T lymphocytes: molecular homology to immunoglobulin and T–cell receptor variable and joining regions", *Proc. Natl. Acad. Sci. USA*, 84:4210–4214 (1987).
Nakayama et al., "Intrathymic signalling in immature CD4$^+$ CD8$^+$ thymocytes results in tyrosine phosphorylation of the T–cell receptor zeta chain", *Nature*, 341:651–654 (1989).

(List continued on next page.)

Primary Examiner—Jacqueline M. Stone
Assistant Examiner—Deborah Crouch
Attorney, Agent, or Firm—Marshall, O'Toole, Gerstein, Murray & Borun

[57] ABSTRACT

A mutant non-human mammal lacking expression of the lymphocyte-specific tyrosine kinase p56$^{lck}$. Lck deficient mice possess few peripheral T lymphocytes and a pronounced thymic atrophy. The remaining thymus contains immature thymocytes surrounded by a perturbed thymic microenvironment. p56$^{lck}$ appears to play a crucial role in early thymocyte differentiation.

7 Claims, 14 Drawing Sheets

OTHER PUBLICATIONS

Ohashi et al., "Ablation of 'Tolerance' and Induction of Diabetes by Virus Infection in Viral Antigen Transgenic Mice", *Cell*, 65:305–317 (1991).

Pircher et al., "T Cell tolerance to M1s$^a$ encoded antigens in T cell receptor Vβ8.1 chain transgenic mice", *The EMBO Journal*, 8(3):719–727 (1989).

Rahemtulla et al., "Normal devlopment and function of CD8$^+$ cells but markedly decreased helper cell activity in mice lacking CD4", *Nature*, 353:180–184 (1991).

Roost et al., "An acquired immune suppression in mice caused by infection with lymphocytic choriomeningitis virus", *Eur. J. Immunol.*, 18:511–518 (1988).

Rudd et al., "Molecular Interactions, T–Cell Subsets and a Role of the CD4/CD8:p56$^{lck}$ Complex in Human T–Cell Activation", *Immunological Reviews*, 111:225–266 (1989).

Schmidt–Ullrich et al., "Transfection of the Cd8α gene restores specific target cell lysis: factors that determine the function and the expression of CD8 in a cytotoxic T cell clone", *International Immunology*, 2(3):247–256 (1990).

Schlorle et al., "Development and function of T cells in mice rendered interleukin–2 deficient by gene targeting", *Nature*, 352:621–624 (1991).

Shaw et al., "Short Related Sequences in the Cytoplasmic Domains of CD4 and CD8 Mediate Binding to the Amino–Terminal Domain of the p56$^{lck}$ Tyrosine Protein Kinase", *Molecular and Cellular Biology*, 10(5):1853–1862 (1990).

Shores et al., "Disorganization and restoration of thymic medullary epithelial cells in T cepp receptor–negative scid mice: evidence that receptor–beraing lymphocytes influence maturation of the thymic microenvironment", *Eur. J. Immunol.*, 21:1657–1661 (1991).

Soriano et al., "Targeted Disruption of the c–src Proto–Oncogene Leads to Osteopetrosis in Mice", *Cell*, 64:693–702 (1991).

Tamauchi et al., "CD4$^+$ CD8$^+$ thymocytes develop into CD4 or CD8 single–positive cells in athymic nude mice*", *Eur. J. Immunol.*, 18:1859–1862 (1988).

Tanaka et al., "Effect of Cyclosporin A on rat thymus: time course analysis by immunoperoxidase technique and flow cytofluorometry", *Clin. Exp. Immunology*, 72:216–221 (1988).

Terai et al., "Apoptosis as a Mechanism of Cell Death in Cultured T Lymphoblasts Acutely Infected with HIV–1", *J. Clin. Invest.*, 87:1710–1715 (1991).

Turner et al., "Interaction of the Unique N–Terminal Region of Tyrosine Kinase p56$^{lck}$ with Cytoplasmic Domains of CD4 and CD8 is Mediated by Cysteine Motifs", *Cell*, 60:755–765 (1990).

Van Ewijk et al., "Immunohistology of T cell differentiation in the thymus of H–Y–specific T cell receptor α/β transgenic mice", *Eur. J. Immunol.*, 20:129–137 (1990).

Van Ewijk, "T–Cell Differentiation is Influenced by Thymic Microenvironments", *Annu. Rev. Immunol.*, 9:591–615 (1991).

Veillett et al., "The CD4 and CD8 T Cell Surface Antigens are Associated with the Internal Membrane Tyrosine–Protein Kinase p56$^{lck}$", *Cell*, 55:301–308 (1988).

Veillette et al., "Engagement of CD4 and CD8 Expressed on Immature Thymocytes Induces Activation of Intracellular Tyrosine Phosphorylation Pathways", *The Journal of Experimental Medicine*, 170:1671–1680 (1989).

Wiedmeier et al., "Effect of Ionizing Radiation on Thymic Epithelial Cell Function, I. Radiation–Spared Thymic Epithelial Grafts Expedite the Recovery of T Cell Function in Lethally Irradiated and Fetal Liver Reconstituted Mice", *The Journal of Immunology*, 140:21–29 (1988).

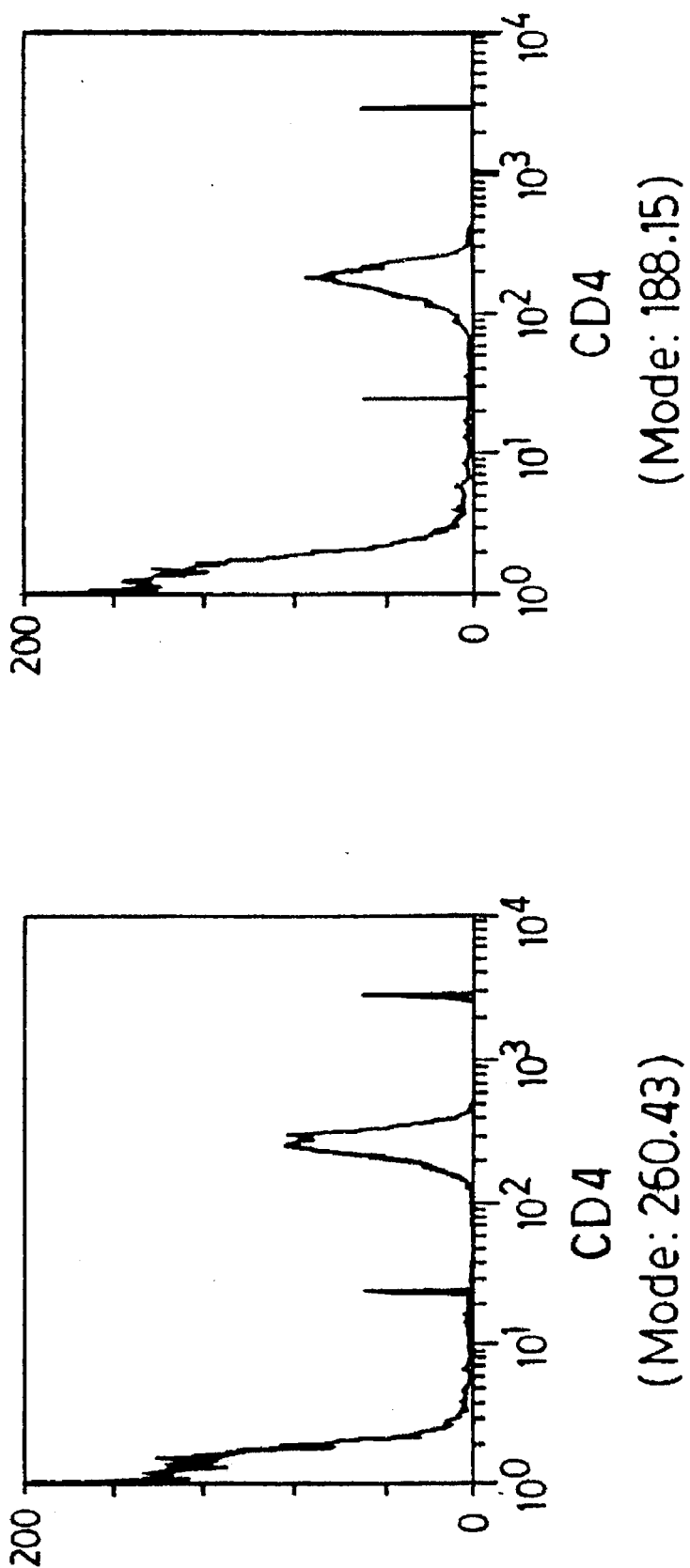

FIG. 3o
Lymph Nodes
+/+
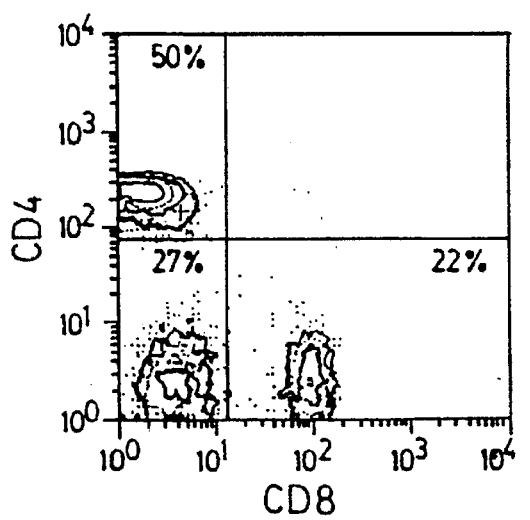
FIG. 3q
Lymph Nodes
-/-
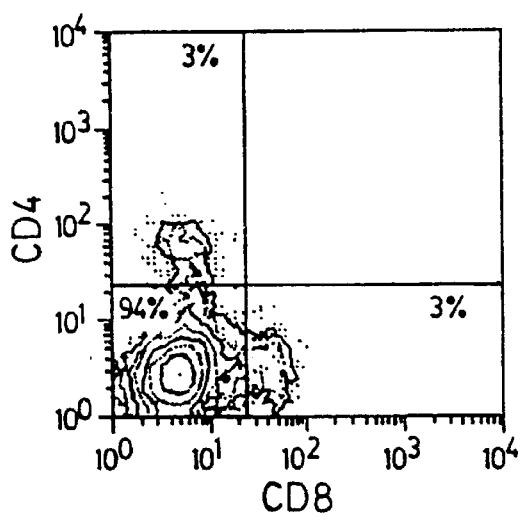
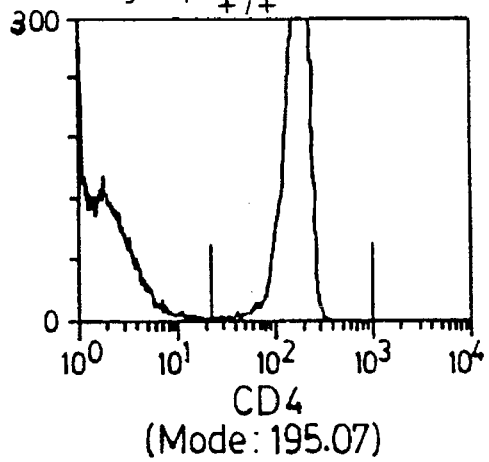
(Mode: 195.07)
FIG. 3p
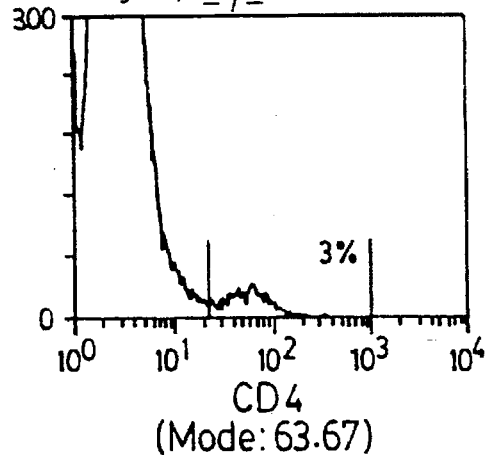
(Mode: 63.67)
FIG. 3r

MOUSE HAVING A DISRUPTED LCK GENE

This application is a continuation of application Ser. No. 07/872,985 now abandoned, filed Apr. 24, 1992.

The invention is a mutant mouse having a disrupted lck gene. The mutant of the invention does not express the lck gene product, lymphocyte-specific tyrosine kinase p56$^{lck}$. The invention is useful for the study of T cell maturation and activation, and accordingly, may prove useful in developing treatments for a wide variety of immune-related diseases.

The lck gene product p56$^{lck}$ is a 56 kilodalton (kD) polypeptide belonging to the Src family of membrane-bound tyrosine protein kinases. Normally, lck is expressed exclusively in lymphoid cells, most predominantly in thymocytes and peripheral T cells. p56$^{lck}$ has been shown to associate specifically with the cytoplasmic domains of both CD4 and CD8 T cell surface glycoproteins, and interact with the IL-2 receptor β-chain and the protein tyrosine phosphatase CD45. These associations suggest that Lck enzymatic activity plays a role in signal transduction during the thymic education of maturing thymocytes and T cell receptor-mediated activation of mature T cells. Moreover, the presence of p56$^{lck}$ in NK cells, EBV-transformed B cell lines, and non-lymphoid carcinoma cell lines, suggests that Lck might also be involved in signal transduction pathways of other cell lineages as well.

Two other Src-related tyrosine protein kinases are expressed in T cells: p59$^{fyn}$ and p62$^{yes}$. Fyn is ubiquitously expressed but exists as an alternative-splicing gene product (p59$^{fynT}$) specific to hematopoietic cells, including T cells. The ability to co-immunoprecipitate p59$^{fynT}$ with the T cell receptor (TCR)/CD3 complex has implicated this kinase in T cell receptor signalling. Moreover, thymocytes derived from transgenic mice overexpressing fyn show an augmented calcium influx response upon TCR engagement[1]. The high degree of conservation between members of the Src family of tyrosine protein kinases[2] and the paucity of abnormalities observed in Src-deficient mice[3] have raised the question of functional redundancy among these kinases and, specifically, whether there is an absolute requirement for both fyn and lck expression during T cell development and activation.

The generation of an lck null mutation by homologous recombination in embryonic stem cells was undertaken to evaluate the role of p56$^{lck}$ in thymocyte development and T cell activation. Lck-deficient mice showed a pronounced thymic atrophy, with aberrant organization of the cortical epithelium and dramatic reductions in both the double positive (CD4$^+$CD8$^+$) thymocyte population and the thymic medullary compartment. Mature, single positive thymocytes were not detectable in these mice and only very low numbers of phenotypically abnormal T cells were found in the periphery. These results not only emphasize the crucial role of p56$^{lck}$ in the early phases of thymocyte development, but also illustrate that an impairment of T cell differentiation (via an intrinsic T cell defect) can influence the development of the thymic microenvironment. The similarities between the perinatal normal thymus and the thymic phenotype observed in these Lck-deficient mice, as well as the abnormal presence of an early thymocyte marker in these mice, raises the possibility that the observed block in thymocyte differentiation occurs at the transition between fetal and postnatal T cell development.

Generation of Mice Lacking p56$^{lck}$

Figure 1A:
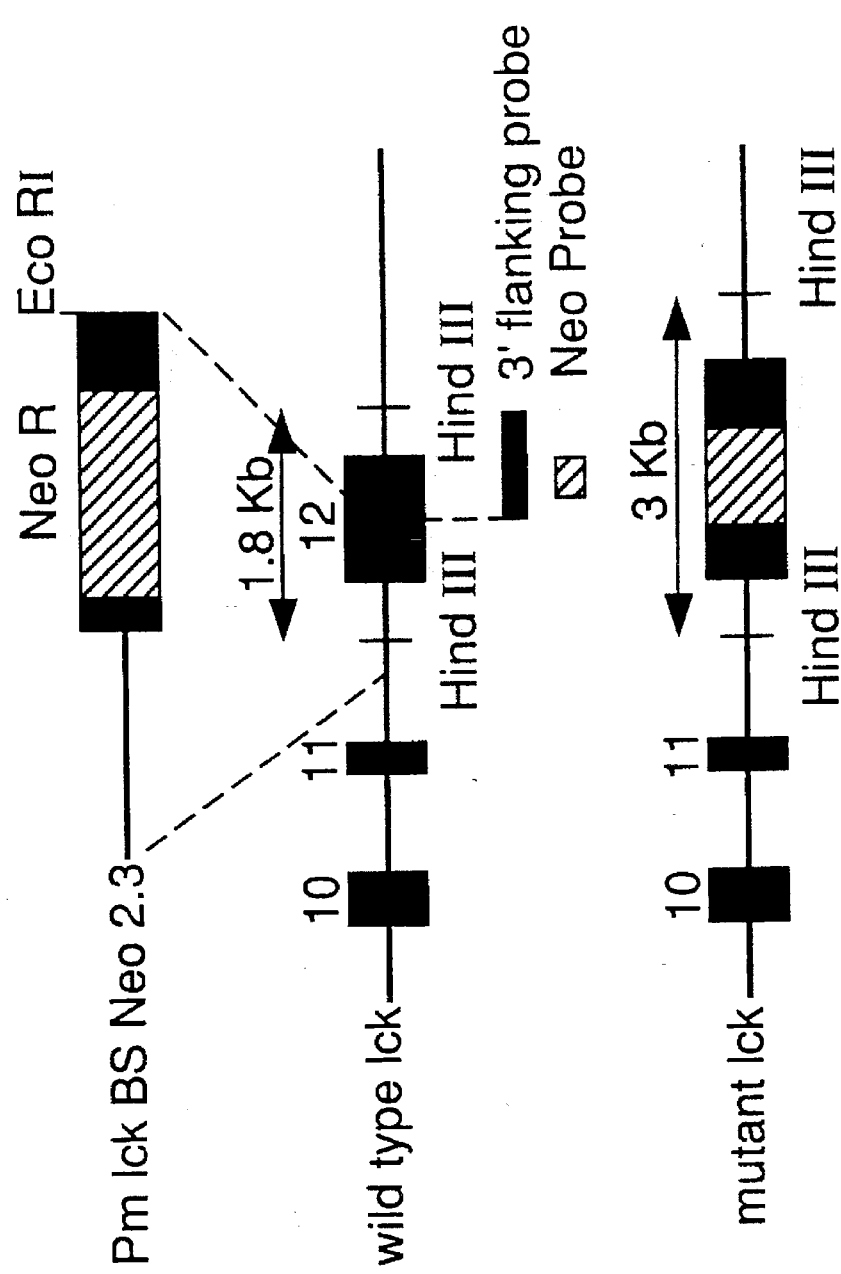
FIG. 1a shows schematic diagrams of the mouse lck locus in parental D3 cells (wild-type lck), the targeting vector (PmlckBSNeo2.3), and the predicted structure of the disrupted lck locus (mutant lck).
Figure 1B:
FIG. 1b is a Southern blot analysis of the structure of the lck locus in parental D3 cells (ES) and two targeted cell lines (56b3 and 5gb5).

A replacement-type vector (PmlckBSNeo2.3) was constructed (FIG. 1a). This targeting vector was introduced into D3 embryonic stem (ES) cells by electroporation. Six independent targeted ES cell lines were generated. The average frequency of homologous recombination was about 1 in 2×10$^7$ electroporated cells and 1 in 130 G418-resistant clones. Southern blot analysis confirmed the homologous recombination event (FIG. 1b). The same profile of hybridization was observed using the targeting vector as a probe, whereas probing with the neomycin resistance gene showed only the single 3 kb fragment (data not shown). Germ-line transmission of the lck disruption was obtained with two ES cell lines. Heterozygous mice were inbred to obtain mice homozygous for the disrupted lck gene.

Homozygous mutant mice have no detectable p56$^{lck}$

Although mice homozygous for the disrupted lck gene are predicted to be unable to produce wild-type p56$^{lck}$ polypeptides, it was conceivable that part of the Lck protein amino-terminal to the mutation could still have been expressed. To address this issue, western blots were performed using an antibody directed against the N-terminal end of Lck, using either thymic (FIG. 2a) or lymph node cell lysates (data not shown). While full-length p56$^{lck}$ was detected in extracts prepared from either wild-type or heterozygous mutant mice (lanes 2–9), no Lck protein, either normal or truncated, was detected in the homozygous mutant mice (lane 1). Immune complex kinase assays (FIG. 2b) demonstrated a 50% decrease in p56$^{lck}$ kinase activity in heterozygous mice (in correlation with 50% of the normal protein level present) and no detectable p56$^{lck}$ kinase activity in the homozygous mutant mice. Thus, the mutation created in these mice is "null": no Lck protein is detected by either structural or functional assays.

CD4 downregulation in heterozygous mutant mice

Heterozygous mutant mice were found to be healthy and their lymphoid organs were normal according to macroscopic examination. Thymocyte and peripheral T cell populations were also normal in these mice. However, CD4 staining of peripheral blood lymphocytes showed a consistent decrease in the fluorescence intensity (mode), suggesting a downregulation of CD4 surface expression in the heterozygous mice (FIG. 3a). Interestingly, this decrease of CD4 expression was not seen on CD4+ thymocytes, nor was there a downregulation of CD8 on either CD8+ thymocytes or CD8+ peripheral T cells (data not shown).

Profound block of thymocyte development in homozygous mutant mice

Mice homozygous for the lck disruption were noted to be healthy and fertile in an animal colony under specific pathogen-free (SPF) conditions. Gross inspection of the lymphold organs showed a considerable atrophy of the thymus, whereas the spleen and lymph nodes were normal in size.

The thymic atrophy observed in these mice is associated with a decrease in the total number of thymocytes ($6 \times 10^6$–$2 \times 10^7$ vs $2 \times 10^8$ for normal littermates). The remaining population consists of 60–80% double positive (CD4+CD8+) and 20–40% double negative (CD4−CD8−) thymocytes. The absolute number of double negative thymocytes is similar to that of normal littermates ($3 \times 10^6$–$6 \times 10^6$); however, there is a dramatic reduction of the double positive thymocyte population ($0.3 \times 10^7$–$1.6 \times 10^7$ vs $1.8 \times 10^8$ for normal littermates). The size of this double positive population remained within these values from 10 days to 8 weeks old. Neither CD4+CD8− nor CD4−CD8+ single positive thymocytes were detectable in the thymi of homozygous mutant mice (FIG. 3b).

The double negative thymocyte population is Thy-1+ CD3$^{low-intermediate}$, with the presence of a J11d$^{high}$, IL-2 receptor α-chain (IL-2Rα) positive subpopulation (40% of double negative thymocytes). The double positive thymocyte population does not contain CD3$^{low}$ cells and there is, on average, elevated CD3 expression at intermediate to high levels: 25% of the CD3+ cells have a CD3 surface expression level similar to that of normal CD3$^{high}$, single positive thymocytes (FIG. 3b).

Surprisingly, among the few thymocytes remaining, 15–20% of the cells from 4 week-old homozygous mutant mice were shown to express an early thymocyte antigen, as assessed by both fluorescence-activated cell sorting (FACS; data not shown) and immunohistochemical staining using the monoclonal antibody Th V-14 (FIG. 4; c vs f). The hybridoma expressing Th V-14 was obtained after fusion of Lou rat spleen cells, previously immunized with fetal C57BL6 thymus cells, with SP2/OF cells. Th V-14-positive thymocytes are first detectable in the thymi of normal mice at gestation day (GD) 13 and, at GD 16, most thymocytes are Th V-14-positive. Later than GD 16, the number of Th V-14-positive thymocytes in normal mice decreases rapidly such that only few positive cells remain, predominantly in subcapsular and cortical regions, after GD 18 and throughout life.

The lack of detectable single positive thymocytes suggests that Lck-deficient thymocytes cannot progress beyond the double positive stage of differentiation. The drastic reduction seen in the size of the double positive thymocyte population may result from a block in the expansion of this cell population, related to their inability to enter the cell cycle. An analysis of the cell cycle using propidium iodide staining[32] of thymocytes from 4 week-old homozygous mutant mice showed a cell-cycle profile similar to that for normal 3–4 week-old littermates (+/+): around 20% of thymocytes are in the S or G2+M phase of the cell cycle (data not shown). Thus, it appears that the reduction in the size of the double positive thymocyte population of Lck-deficient mice is not the result of a block in cell cycle entry. It remains unresolved whether this reduction is caused by increased thymocyte apoptosis or a block in thymocyte differentiation prior to a programmed or thymic-induced expansion of the double positive population, or both.

Perturbation of the thymic microenvironment

The developmental block observed within the thymocyte population is also evident within the thymic architecture. Immunohistochemical staining of the thymus using the cortical epithelium-specific monoclonal antibody ER-TR4 showed that the normal reticular organization of the cortical stromal cells was disrupted in the homozygous mutant mice (FIG. 4; a vs d). Although single positive thymocytes are undetectable in homozygous mutant mice, small zones of thymic medulla were detected by conventional histology (hematin-eosin staining; data not shown). Immunohistochemical staining using the monoclonal antibody ER-TR5 confirmed that few medullary epithelial cells were present, but only within very restricted loci, as compared to normal mice (FIG. 4; b vs e). Together, these data indicate that the abnormal T cell development observed in these Lck-deficient mice is paralleled by an abnormal development of the thymic stroma.

Abnormal peripheral T cells

Figure 3C:
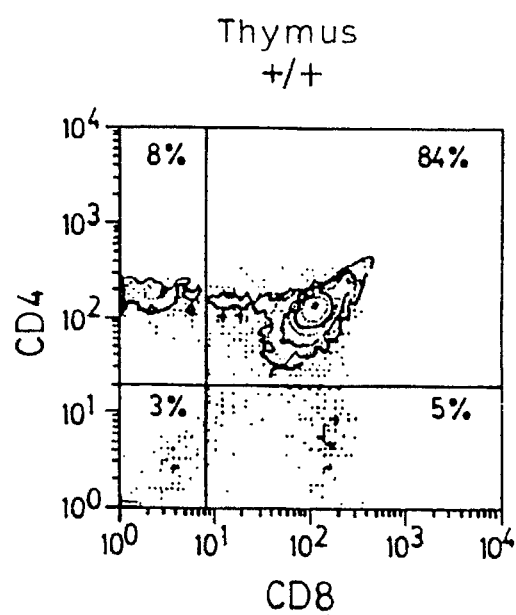
FIGS. 3a–3t represent flow cytometric analysis of peripheral blood (FIGS. 3a–3b); thymocytes (FIGS. 3c–3h); and lymph node cells (FIGS. 3i–3t) from 3–4 weeks old wild type (+/+), heterozygous (+/−), and homozygous (−/−) mutant mice cloned from 5gb5ES cell line.
Figure 3E:
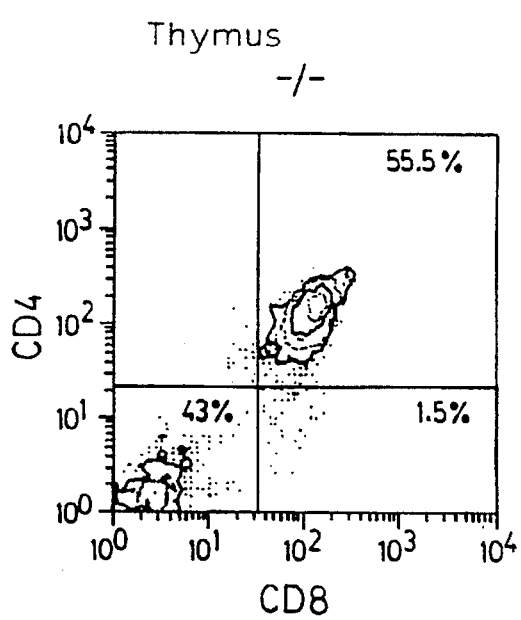
Figure 3D:
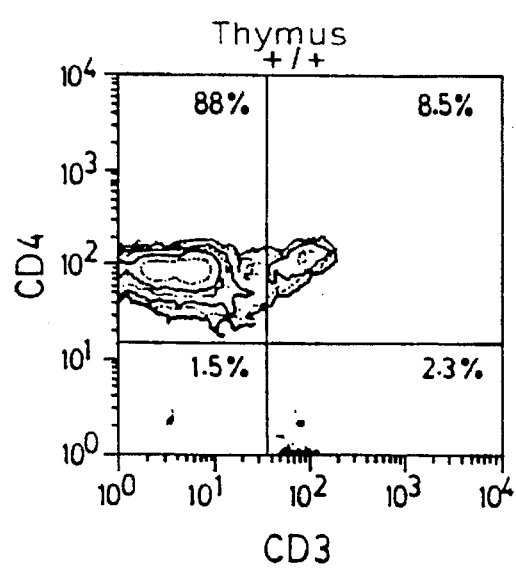
Figure 3F:
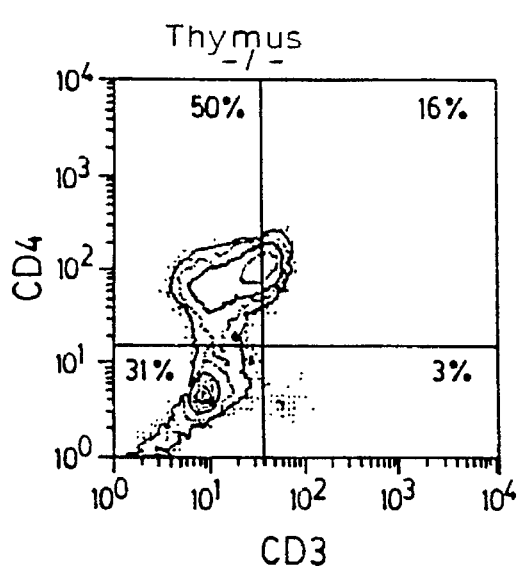
Figure 3G:
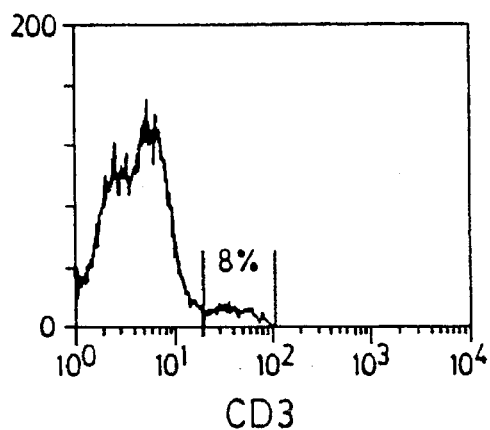
Figure 3H:
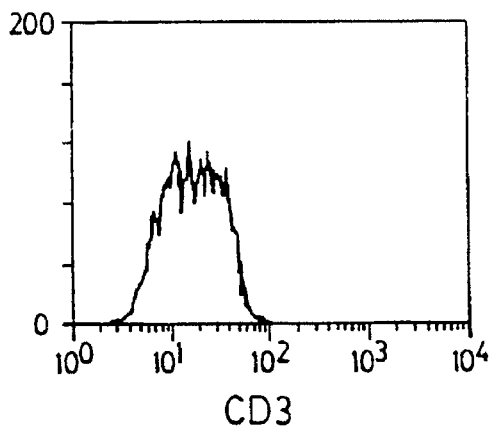
Figure 3I:
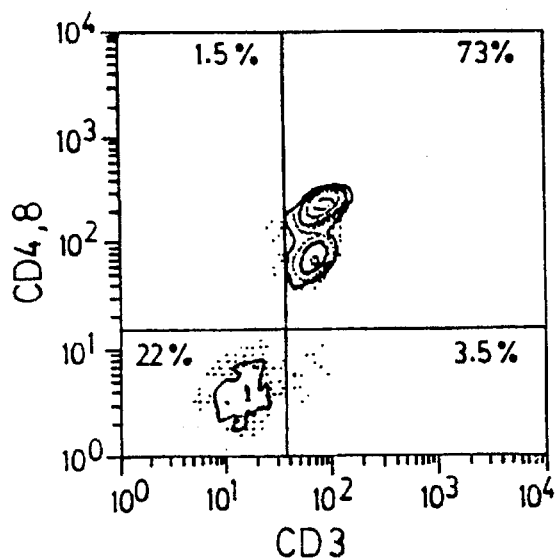
Figure 3J:
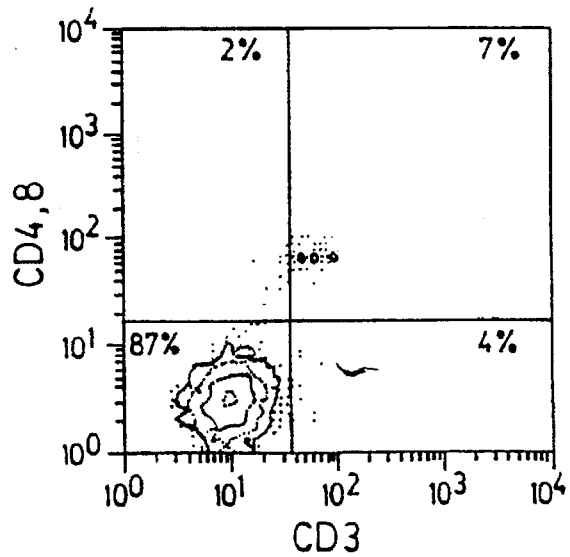
Figure 3K:
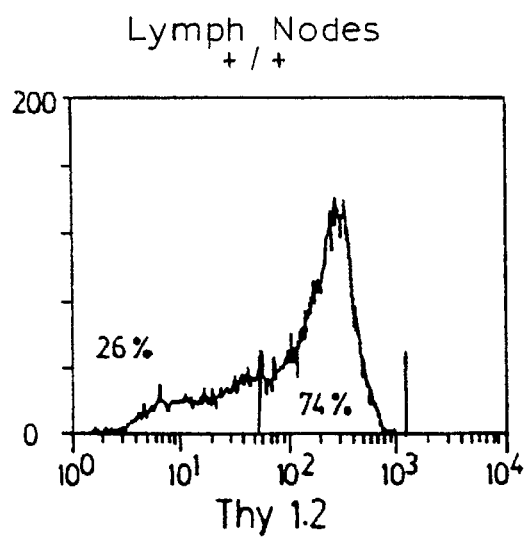
Figure 3M:
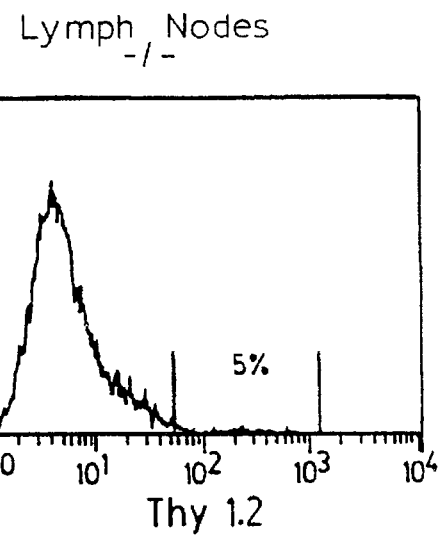
Figure 3L:
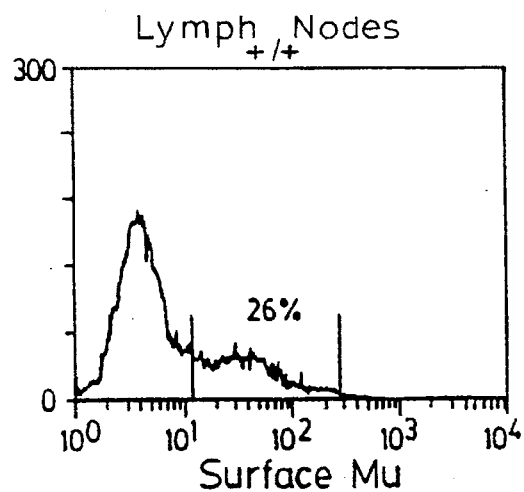
Figure 3N:
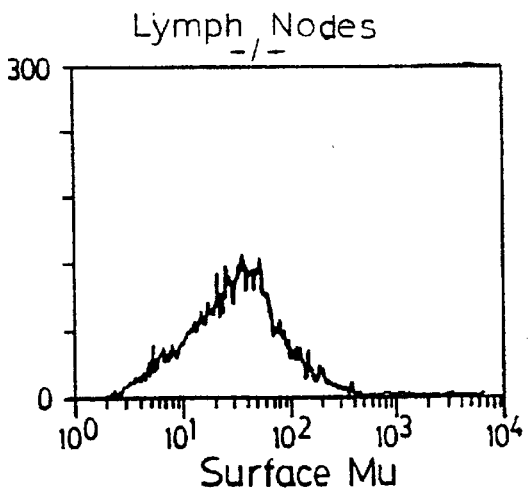
Figure 3S:
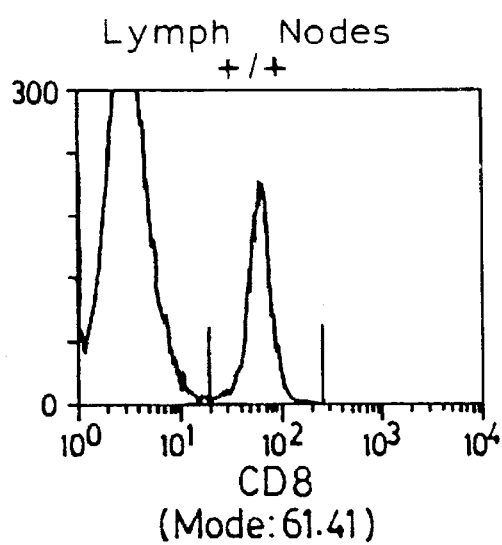
Figure 3T:
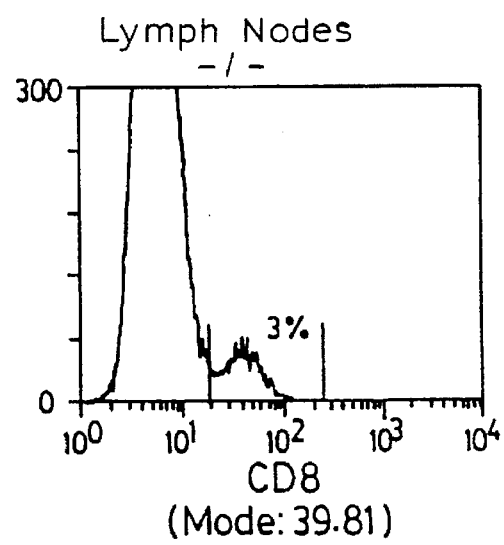
Figure 4A:
FIGS. 4a–f show thymic immunohistology of (a–c) normal and (d–f) Lck-deficient mutant mice, stained with the monoclonal antibodies (a,d) ER-TR4, detecting cortical epithelial cells, (b,e) ER-TR5, detecting medullary epithelial cells, and (c,f) Th V-14, detecting an early thymocyte antigen (ca, thymic capsule; C, cortex; M, medulla). Frozen sections of thymi from 3–4 week old normal and homozygous mutant mice were stained with different antibodies using a two-step immunoperoxidase method as previously described[17].
Figure 4B:
Figure 4C:
Figure 4D:
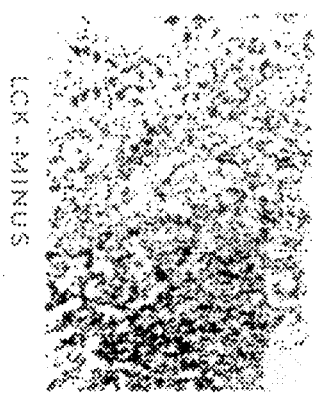
Figure 4E:
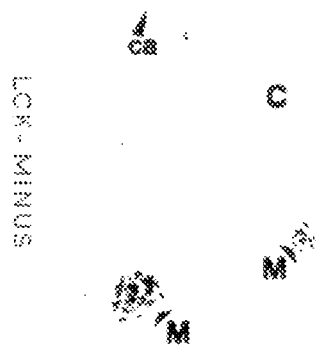
Figure 4F:
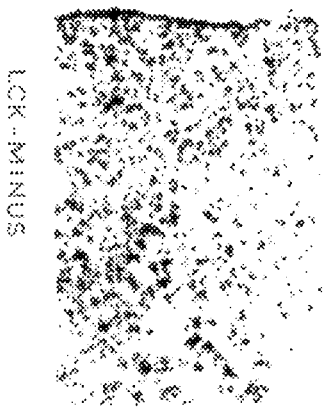

Although the overall numbers of cells within lymph nodes and spleens from homozygous mutant mice are normal, a dramatic inversion in the B/T cell ratio was observed: 90 to 95% B cells and 5 to 10% T cells (FIG. 3c). Peripheral T cells are Thy-1+, CD3+, TCRαβ+, and display a lowered surface expression of either CD4 or CD8 (Lyt2–Lyt3 heterodimer; FIG. 3d). One percent of the lymph node population are TCRγδ+ T cells.

Figure 5:
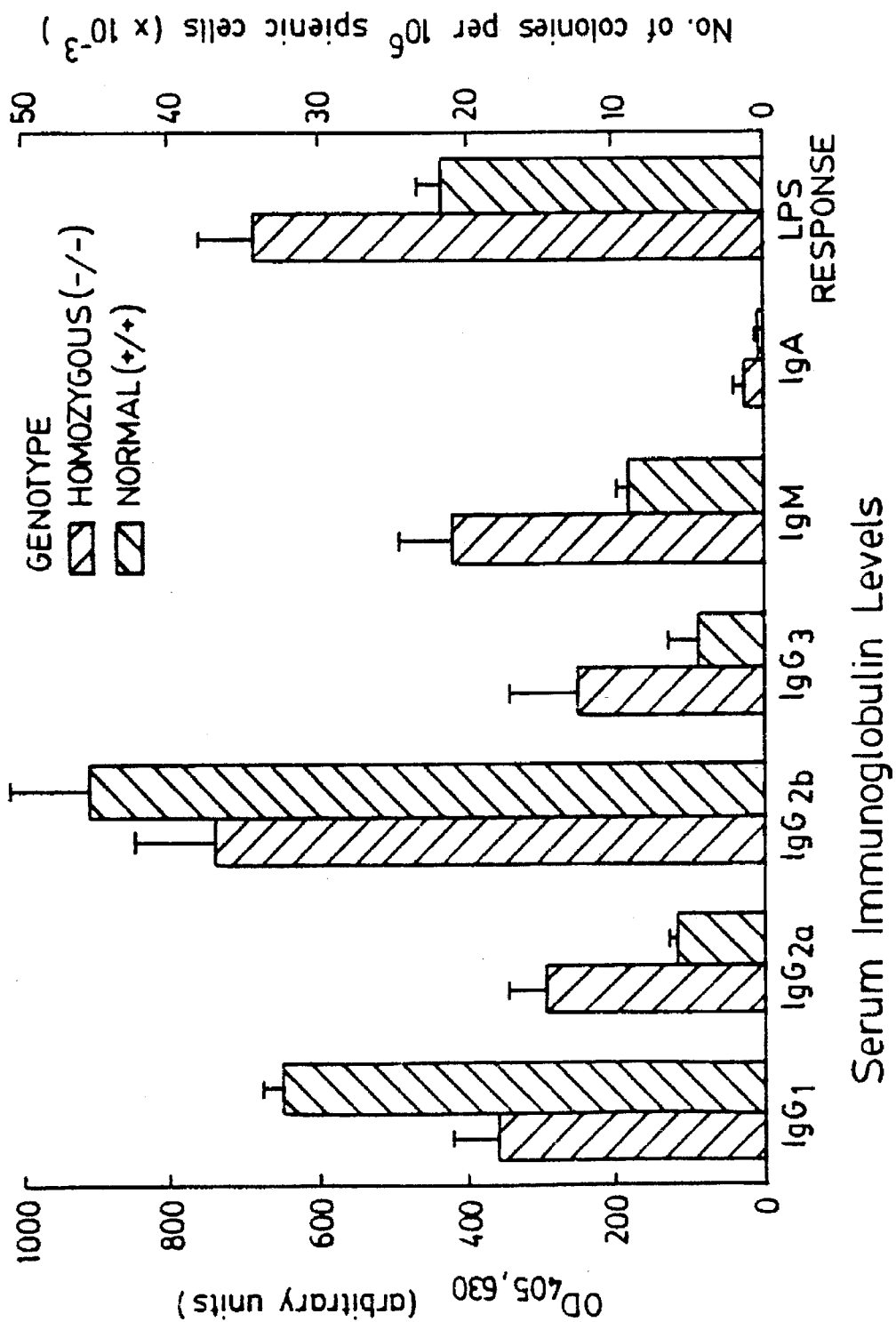
FIG. 5 is a graph showing proliferative responses of peripheral T cells from normal (+/+) and Lck-deficient (−/−) mice.

To test the activation signaling pathways in those few T cells found in the periphery, lymph node and spleen, T cells were purified and stimulated using anti-CD3 or anti-TCRαβ monoclonal antibodies, interleukin-2 (IL-2), phorbol ester (PMA) and calcium ionophore (ionomycin; FIG. 5). Proliferative responses were assessed by [$^3$H]-thymidine uptake and were identical in normal and heterozygous mutant mice for all stimulants tested (data not shown). In the homozygous mutant mice, there is a proliferative response to both CD3 and TCRαβ crosslinking, but this response is reduced as compared to control, especially for CD3. Response to CD3 crosslinking in the presence of IL-2 was consistently higher than to CD3 alone, and the response to IL-2 alone was within the same range as the control. The responses to phorbol ester and ionomycin treatment were identical for normal and Lck-deficient T cells.

B cell responses

Figure 6:
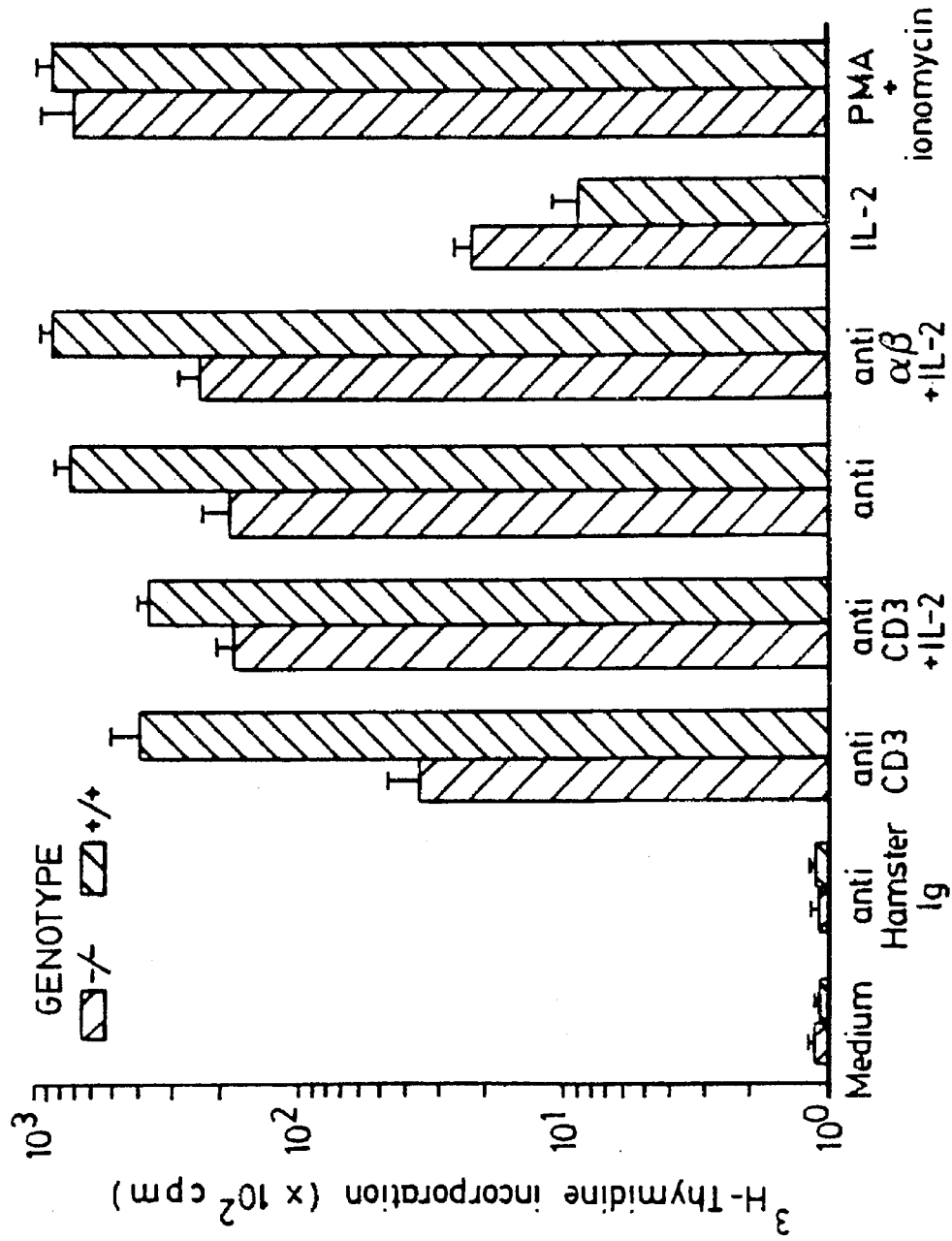
FIG. 6 is a graph showing analysis of B cell responses in normal (+/+) and Lck-deficient (−/−) mice.

Evaluation of serum immunoglobulin levels by a modified ELISA procedure revealed an increase in IgM, a significant decrease in IgG$_1$, and a marginal increase in IgG$_{2a}$ and IgG$_3$ isotypes in homozygous mutant mice (FIG. 6). However, the competence of splenic B cells from these Lck-deficient animals to respond to the T-independent mitogen LPS was found to be comparable to that of normal mice (FIG. 6).

Discussion

Mice lacking p56$^{lck}$ have a profound block in thymocyte differentiation and few peripheral T cells, demonstrating that p56$^{lck}$-mediated signals are required for progression beyond the double positive (CD4+CD8+) thymocyte stage. The potential role of p56$^{lck}$ in T cell development had been suggested by lck transgenic mice models, in which a loss of mature, functional CD3+ thymocytes was observed upon augmented expression of p56$^{lck}$ (ref. 4). The strong impairment in T cell development observed in the Lck-deficient mice underlines the crucial role of this kinase, since the other T cell-specific tyrosine kinases, fyn and yes, are unable to compensate for the absence of lck. This lack of functional redundancy, at least for lck activity, is surprising in light of the functional overlap observed in other tyrosine kinase-deficient mouse strains. Mice lacking c-src possess no apparent abnormalities in tissues normally expressing high levels of c-src (i.e., platelets and neurons; ref. 3); moreover, mice lacking fyn display normal thymocyte development and normal peripheral immune responses, although the proliferative response and calcium mobilization after CD3-crosslinking is diminished in Fyn-deficient thymocytes.

Lck-deficient mice not only possess a thymocyte developmental defect, but this block is also seen to perturb the thymic architecture. Although the reduction in thymic medulla can be partially explained by the absence of single positive thymocytes, the paucity of medullary epithelial cells and the disordered appearance of the cortical stromal cells are thought to result from the lack of interaction with developing thymocytes. The observation that impaired T cell differentiation (caused by an intrinsic T cell defect) can influence the development and structure of the thymic microenvironment indicates that the interaction between thymic lymphoid and stromal components is symbiotic and not, as previously thought, a one-way instruction from the thymic microenvironment to the developing T cell[5]. Reduction of the ER-TR5+ medullary stromal compartment has also been observed in mice exposed to other lymphold-depleting regimens (i.e., cyclosporin A[6,7], ionizing radiation[8,9]), and in SCID mice, which lack functional B and T cells[10]. The ability to restore both the thymic architecture and T cell differentiation upon reconstitution of SCID mice with normal bone marrow cells[11] supports the notion that the medullary microenvironment itself is influenced by the presence of developing thymocytes.

Although there is a strong impairment in T cell and thymic development, B cells, colon, and lung appear to develop normally in Lck-deficient mice, indicating that lck expression is not essential for the development of these cell lineages and suggesting that the expression of lck in immortalized B cell, colonic, and pulmonary carcinoma cell lines reflects an aberrant regulation of lineage-specific gene expression in transformed cells. The normal response of splenic B cells to LPS and the presence of IgM in the serum demonstrate that the lack of lck does not interfere significantly with T-independent B cell function. The increased serum IgM levels observed in the homozygous mutant mice may simply be due to the higher absolute number of B cells found in these animals or may rather reflect a perturbation in the activity of distinct B cell populations, such as the Ly1+ B cell subpopulation, which are thought to contribute to the production of natural antibodies. The significant decrease of IgG$_1$ levels in the homozygous mutant mice, but not of other immunoglobulin isotypes, may be related to the low number of CD4$^{low}$ T cells present in the periphery, potentially responsible for a decreased efficiency of immunoglobulin class-switching and creating an immunoglobulin profile in the Lck-deficient mice comparable to that seen in the absence of T-helper cell function (i.e., MHC class II-deficient mice[12] and IL-4-deficient mice[13]).

Despite the strong abnormalities in T cell development, Lck-deficient peripheral T cells are present, albeit in dramatically reduced numbers. Interestingly, these cells can signal through the TCR-CD3 complex. There is a proliferative response to both CD3- and TCRαβ-crosslinking among these peripheral T cells, demonstrating that lck is not indispensable for the CD3 signaling pathway. The decreased proliferative response relative to normal T cells may have several explanations, including the observed decrease in accessory molecule (CD4/CD8) expression and/or the absence of p56$^{lck}$ as a potential signal amplifier. The enhanced response to CD3- and TCRαβ-crosslinking in the presence of IL-2, and the response to IL-2 alone, suggest that, although shown to coprecipitate with IL-2 receptor β-chain and to be activated upon IL-2 stimulation of human T cells, p56$^{lck}$ is not indispensable for the IL-2 signalling pathway. The normal proliferative response observed using phorbol ester and ionomycin in Lck-deficient peripheral T cells indicates that signal transduction via protein kinase-C activation and calcium influx is already downstream of events mediated by p56$^{lck}$.

In the periphery, there is a decrease in CD4 cell-surface expression which is detected even within heterozygous mutant mice, and a decrease in both CD4 and CD8 expression in homozygous mutant mice. Curiously, however, there is no decrease of CD4- or CD8-expression in the thymus, even among the few double positive thymocytes remaining in homozygous mutant mice. These observations suggest that the role of p56$^{lck}$ in the regulation of CD4 and CD8 surface expression is different in the thymus versus the periphery. Others have indicated that p56$^{lck}$ might be involved in the regulation of CD4 internalization; the down-regulation of CD4 observed in our heterozygous mutant mice also supports this notion, although transcriptional or translational regulation of CD4 expression by p56$^{lck}$ cannot be ruled out.

The extensive degree of interaction between CD4 and p56$^{lck}$ (and also, to a lesser extent, CD8 and p56$^{lck}$) in double positive thymocytes, as well as the observed enhancement of lck kinase activity upon CD4-crosslinking, suggests that the thymic atrophy and impairment of thymocyte maturation in the Lck-deficient mice is related to an inability of CD4 and/or CD8 to transduce their signals. The crucial role of CD4 and CD8 during positive and negative selection is well established; however, mice lacking either CD4, CD8, or both CD4 and CD8 have normal thymic architectures and no decrease of the total number of thymocytes[14,15]. Therefore, an inability to signal through CD4 or CD8 cannot be considered the main factor responsible for the thymocyte developmental defect in Lck-deficient mice.

Thymocyte kinetic studies have indicated that thymocyte maturation comprises both thymocyte expansion and cellular differentiation; yet, positive selection does not seem to involve a significant expansion of the double positive population. Whereas CD4- and CD8-mediated signals are considered important during positive selection, the signalling pathway involved in the prior phase of expansion of the double positive thymocyte population is currently unknown. The drastic reduction in the number of double positive thymocytes observed in Lck-deficient mice implicates p56$^{lck}$ in the signalling pathway required for this expansion phase. Furthermore, interaction of p56$^{lck}$ with the IL-2 receptor β-chain could be considered important for this expansion signal, although mice lacking IL-2 display no thymocyte developmental defect[51]. p56$^{lck}$ interaction with GPI-anchored cell-surface molecules such as Thy-1 and/or the protein tyrosine phosphatase CD45 might also be required for this expansion signal. However, the observed lack of double positive thymocyte expansion in Lck-deficient mice does not exclude the possibility that p56$^{lck}$-mediated signals are also important during thymic selection and, therefore, the analysis of a specific T cell receptor transgene in Lck-deficient mice should bring some insights into positive and negative selection signalling events.

Intriguingly, in the 4–6 week-old homozygous mutant mice, the thymic phenotype is very similar to the perinatal normal thymus during the transitional phase between the two major waves, fetal and postnatal, of thymocyte development. The small size of the thymocyte population (~$10^7$ cells), the proportion of double positive (80%) and double negative thymocytes (20%), and the cell cycle profile are surprisingly similar. Moreover, Lck-deficient adult mice possess thymocytes expressing an antigen normally seen on fetal thymocytes (Th V-14), as well as immature thymic stromal compartments. These observations suggest that, in the absence of lck expression, thymocyte maturation is arrested at a perinatal stage of development p56$^{lck}$ mediated tyrosine phosphorylation may thus provide the required signal for progression into the postnatal phase of thymic development, directing the expansion of the double positive thymocyte population.

Experimental Methods

Production of Mutant Mice Homozygous for the Disrupted lck Gene

A targeting vector, PmlckBSNeo2.3, was constructed. The neomycin resistance gene (Neo R) cassette containing 1.2 kilobases (kb) derived from the XhoI-SalI fragment of plasmid pMC1PolA (ref. 18) and was inserted in a SalI site created at a previous BspMII site in exon 12 of the lck gene, 110 bp upstream of the codon corresponding to tyrosine-505. The 2.3 kb of genomic lck in the targeting vector was obtained by screening of a mouse genomic library with a human lck cDNA probe. Electroporation of the D3 ES cells and screening for homologous recombination were carried out according to Joyner et al.[19]. A primer specific for the neo cassette within the neomycin resistance coding sequence (5'-TATCAGGACATAGCGTTGGCTACCC-3'), and another antisense primer specific for exon 12 of lck, 3' of the targeting vector (5'-CTTAGACTCACGTGCTCCACAGGTA-3'), were used in the polymerase chain reaction (PCR) performed to detect homologous recombination; lck cDNA sequences spanning exon 12 were used as a probe in this PCR detection method (data not shown).

A Southern blot was performed comparing the structure of the lck locus in parental D3 ES cells and two targeted cell lines 56b3 and 5gb5. Genomic DNA was digested with HindIII and probed using the 3' flanking probe (600 bp EcoRI-HindIII fragment). In cases of homologous recombination, a 3 kb fragment is detected from the disrupted lck allele, instead of a 1.8 kb from the wild-type allele.

Mice heterozygous for the mutant gene were inbred to homozygosity.

Analysis of p56$^{lck}$ expression and activity

Figure 2A:
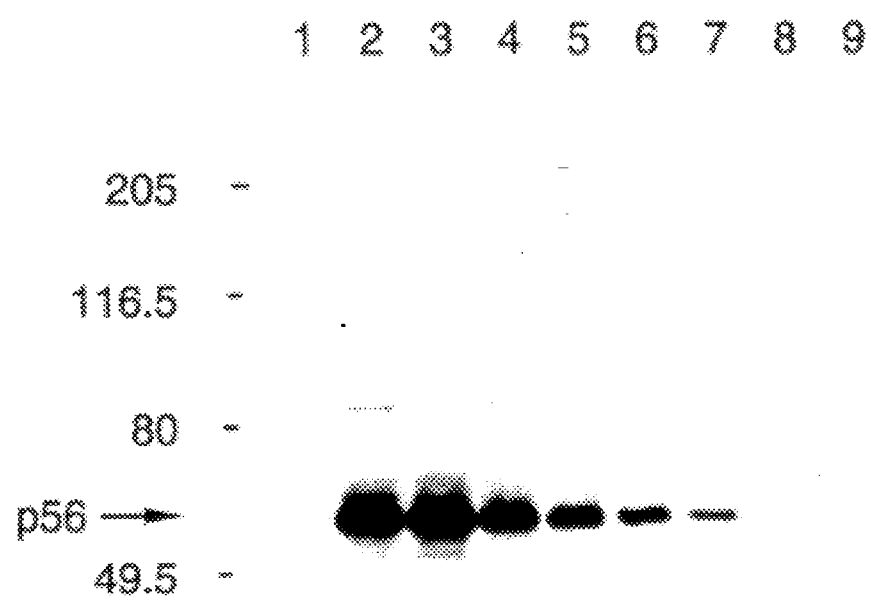
FIG. 2a is an immunoblot analysis of p56$^{lck}$ protein levels.

FIG. 2a shows an immunoblot analysis of p56$^{lck}$ protein levels of 100 μg thymocyte lysates from homozygous mutant (−/−; lane 1), heterozygous mutant (+/−; lane 2), and wild-type mice (+/+; lane 3); lanes 4–9, titration of wild-type (+/+) thymocyte lysate, 50, 25, 12.5, 6.25, 3.12, and 1.6 μg, respectively. Autoradiograph exposure time: 15 h. Quantitation of the bands revealed that the amount of p56$^{lck}$ in the heterozygous mutant mouse cell lysate (lane 2) was approximately half of the amount in wild-type mouse lysate (lane 3).

Figure 2B:
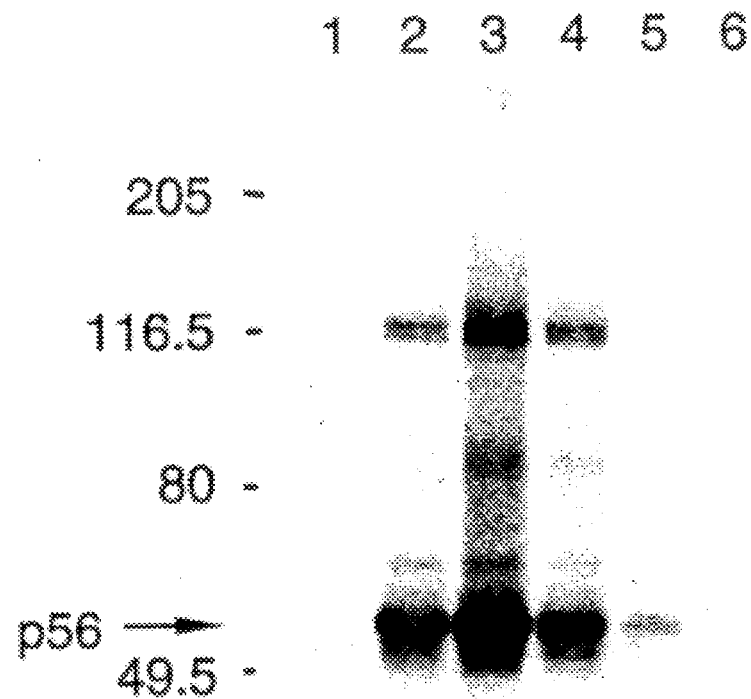
FIG. 2b is an immune complex kinase assay of p56$^{lck}$ activity.

FIG. 2b shows an immune complex kinase assay of p56$^{lck}$ activity. The tyrosine kinase activity of p56$^{lck}$ (autophosphorylation) was assessed using Lck immunoprecipitates from cell lysates: 150 μg thymocyte lysates from homozygous mutant (−/−; lane 1), heterozygous mutant (+/−; lane 2), and wild-type mice (+/+; lane 3); lanes 4–6, titration of the wild-type (+/+) thymocyte lysate, 75, 37.5, and 18.8 μg, respectively. Autoradiograph exposure time: 15 h. Quantitation revealed that the kinase activity in the heterozygous mutant mouse cell lysate (lane 2) was approximately half of the wild-type activity (lane 3). Positions of markers of known molecular weight and the position of p56$^{lck}$ are indicated on the left of each figure. METHODS Immunoblot analysis. Thymic and lymph nodes cells of 3–4 weeks-old mice were washed in PBS and Lysed in TNE buffer (50 mM Tris pH8.0, 1% NP-40, 2 mM EDTA pH8.0) supplemented with protease inhibitors and phosphatase inhibitors. Defined amounts of proteins from cellular lysates were denatured in sample buffer, boiled, and resolved by 8% SDS-PAGE. The proteins were electrophoretically transferred to nitrocellulose and analysed for p56$^{lck}$ expression using a rabbit antiserum generated against a fusion protein containing amino acids 2–148 of the murine p56$^{lck}$ sequence. Bands were cut from the nitrocellulose blot and counted in a y-counter for quantitation.

Immune complex kinase assay. p56$^{lck}$ was recovered from cell lysates using a rabbit anti-Lck antiserum directed against amino acids 39–64. After collection on formalin-fixed Staphylococcus aureus (Pansorbin, CalBiochem), immune complexes were washed and resuspended in kinase buffer. Kinase reactions were performed for 2 minutes at room temperature with constant shaking in 25 μl of kinase buffer containing 1 μM of cold ATP, 12.5 μCi [γ-$^{32}$P]-ATP (3000 Ci/mmol, New England Nuclear). Reactions were stopped by the addition of 1 ml lysis buffer, washed three times, and resuspended in sample buffer. Phosphorylated polypeptides were subsequently resolved on 8% SDS-PAGE gels.

Flow Cytometric Analysis

Single-cell suspensions from red-blood cell-depleted peripheral blood, thymus, and lymph nodes were made and 2–5×$10^5$ cells were stained with monoclonal antibodies for 45 min at 4° C. in 100 μl PBS containing 1% BSA and 0.1% sodium azide. Cells were then washed with PBS and analysed by double-colour flow cytometry on a FACScan (Becton Dickinson). Monoclonal antibodies used were anti-Lyt-2 (53-6.7, Becton Dickinson), anti-L3T4 (GK1.5, Becton-Dickinson), anti-CD3 (145-2C11, PharMingen), anti-Thy 1.2 (30H12, PharMingen), and anti-surface mu (Sigma).

Proliferative responses of peripheral T cells from normal (+/+) and Lck-deficient (−/−) mice Nylon wool purified lymph node and splenic T cells from normal, heterozygous (data not shown), and homozygous mutant mice were cultured in flat-bottomed, 96-well plates at a concentration of 5×$10^4$ T cells/well (as measured by Thy-1 and CD3 staining on FACScan). Crosslinking experiments were performed using plate-bound antibody stimulation and $10^6$ irradiated (3000 rads) spleen cells were added. Prior to stimulation with anti-CD3 (2C11) and anti-TCRαβ (H57-597) antibodies, plates were coated overnight with purified rabbit anti-hamster IgG (10 μg/mL). Concentrations used: 20 units/mL recombinant interleukin-2 (rIL-2, Roche), 10 ng/mL phorbol 12-myristate 13-acetate (PMA, Sigma), and 400 mng/mL ionomycin (CalBiochem). The cells were cultured for 3 days in IMDM (10% FCS) and cultures were pulsed with 1 μCi of [$^3$H]-thymidine on day 3 and harvested 9 hours later. Values plotted in FIG. 5 represent mean of triplicate cultures ± standard deviations (SD). This experiment is representative of four different experiments performed.

Analysis of B cell responses in normal (+/+) and Lck-deficient (-/-) mice.

The amount of various immunoglobulin isotypes in 5 weeks old homozygous mutant (-/-) and age/sex-matched normal (+/+) mice were determined by a panel of mouse isotyping antibodies (Bio-Rad, Calif. Catalog No.172-2055). The assay procedure was carried out essentially as described by the manufacturer, using sera diluted 100 times in PBS. The frequency of LPS-responsive splenic cells was determined by a double-layer agar culture assay. Spleens of homozygous mutant mice contained, on average, approximately 30% more B cells (data not shown). Serum immunoglobulin levels and splenic cell LPS responsiveness were analysed by a modified ELISA and an agar colony assay, respectively.

Deposits

The ES cell lines 56b3 and 5gb5 have been deposited in the American Type Culture Collection, Rockville, Md., and given ATCC Accession Nos. CRL. 11117, CRL. 11115 respectively.

References

1. Cooke, M. P., Abraham, K. M., Forbush, K. A. & Perlmutter, R. M. Cell 65, 281–291 (1991).
2. Cooper, J. A. in Peptides and Protein Phosphorylation (ed. Kemp, B. E.) 85–113 (CRC Press, Boca Raton, 1990).
3. Soriano, P., Montgomery, C., Geske, R. & Bradley, A. Cell 64, 693–702 (1991).
4. Abraham, K. M., Levin, S. D., Marth, J. D., Forbush, K. A. & Perlmutter, R. M. J. exp. Med. 173, 1421–1432 (1991).
5. van Ewijk, W. Ann. Rev. Immun. 9, 591–615 (1991).
6. Tanaka, M., Shinohara, K., Fukumoto, T., Tanaka, H. & Kaneko, T. Clin. exp. Immun. 72, 216–221 (1988).
7. Kanariou, M. et al. Clin. exp. Immun. 78, 263–270 (1989).
8. Wiedmeier, S. E., Samlowski, W. E., Rasmussen, C. J., Huang, K. & Daynes, R. A. J. Immun. 140, 21–29 (1988).
9. Adkins, B., Gandour, D., Strober, S. & Weissman, I. J. Immun. 140, 3373–3379 (1988).
10. Bosma, G. C., Custer, R. P. & Bosma, M. J. Nature 301, 527–530 (1983).
11. Shores, E. W., van Ewijk, W. & Singer, A. Eur. J. Immun. 21, 1657–1661 (1991).
12. Cosgrove, D. et al. Cell 66, 1051–1066 (1991).
13. Kühn, R., Rajewsky, K. & Müller, W. Science 254, 707–710 (1991).
14. Rahemtulla, A. et al. Nature 353, 180–184 (1991).
15. Fung-Leung, W-P. et al. Cell 65, 443–449 (1991).
16. Schorle, H., Holtschke, T., Hunig, T., Schimpl, A. & Horak, I. Nature 352, 621–624 (1991).
17. van Ewijk, W., Kisielow, P. &von Boehmer, H. Eur. J. Immun. 20, 129–137 (1990).
18. Thomas, K. R. & Capecchi, M. R. Cell 51, 503–512 (1987).
19. Joyner, A. L., Skarnes, W. C. & Rossant, J. Nature 338, 153–156 (1989).

I claim:

1. A mouse homozygous for a disrupted lck gene, wherein the lck gene is disrupted by a selectable marker sequence and wherein said mouse has an absence of $CD4^+CD8^-$ and $CD4^-CD8^+$ thymocytes.

2. The mouse of claim 1 wherein the disruption comprises a disruption of exon 12 of the lck gene.

3. The mouse of claim 2 wherein the disruption comprises an insertion of a marker for neomycin resistance into the EcoRI site of exon 12.

4. A mouse homozygous for a disrupted lck gene, wherein the lck gene is disrupted by a selectable marker sequence incorporated into the genome of an embryonic stem cell line having ATCC Accession No. CRL 11115, said embryonic stem cell being introduced into said mammal or an ancestor of said mammal at an embryonic stage; wherein said mouse has an absence of $CD4^+CD8^+$ and $CD4^-CD8^+$ thymocytes.

5. A mouse homozygous for a disrupted lck gene, wherein the lck gene is disrupted by a selectable marker sequence incorporated into the genome of an embryonic stem cell line having ATCC Accession No. CRL 11117, said embryonic stem cell being introduced into said mammal or an ancestor of said mammal at an embryonic stage; wherein said mouse has an absence of $CD4^+CD8^-$ and $CD4^-CD8^+$ thymocytes.

6. Embryonic stem cell line ATCC Accession No. 11115, where said cell line has a disrupted lck gene.

7. Embryonic stem cell line ATCC Accession No. 11117, where said cell line has a disrupted lck gene.

* * * * *

UNITED STATES PATENT AND TRADEMARK OFFICE
CERTIFICATE OF CORRECTION

PATENT NO. : 5,625,122
DATED : April 29, 1997
INVENTOR : Tak W. Mak

It is certified that error appears in the above-identified patent and that said Letters Patent is hereby corrected as shown below:

column 3, line 50, please replace "OF" with --FO--;

column 4, line 22, please replace "loci" with --foci--;

column 5, line 32, please replace "lymphold" with --lymphoid--;

column 7, line 18, after "development" please insert --.--;

column 8, line 22 please replace "y" with --γ--;

column 8, line 61, please replace "mng" with --ng--;

column 9, line 23, please replace "Perimutter" with --Perlmutter--;

column 9, line 29, please replace "Perimutter" with --Perlmutter--; and column 10, line 30, please replace "CD4$^+$CD8$^+$" with --CD4$^-$CD8$^+$--.

Signed and Sealed this

Fourteenth Day of October, 1997

Attest:

BRUCE LEHMAN

*Attesting Officer*  *Commissioner of Patents and Trademarks*